(12) United States Patent
Barnes

(10) Patent No.: US 11,039,934 B2
(45) Date of Patent: Jun. 22, 2021

(54) EXPANDABLE SPINAL FUSION DEVICE AND METHOD

(71) Applicant: BRYAN BARNES PC., Athens, GA (US)

(72) Inventor: Bryan Barnes, Athens, GA (US)

(73) Assignee: BRYAN BARNES PC., Athens, GA (US)

( * ) Notice: Subject to any disclaimer, the term of this patent is extended or adjusted under 35 U.S.C. 154(b) by 201 days.

(21) Appl. No.: 16/308,188

(22) PCT Filed: Jun. 7, 2017

(86) PCT No.: PCT/US2017/036376
§ 371 (c)(1),
(2) Date: Dec. 7, 2018

(87) PCT Pub. No.: WO2017/214284
PCT Pub. Date: Dec. 14, 2017

(65) Prior Publication Data
US 2019/0298539 A1    Oct. 3, 2019

Related U.S. Application Data

(60) Provisional application No. 62/348,750, filed on Jun. 10, 2016.

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/4611* (2013.01); *A61B 2017/0256* (2013.01);
(Continued)

(58) Field of Classification Search
CPC ........ A61F 2/447; A61F 2/4611; A61F 2/442; A61F 2/4425; A61F 2/4455; A61F 2/4637; A61F 2/4603; A61F 2002/30261; A61F 2002/4629; A61F 2002/30482; A61F 2002/30538; A61F 2002/30556;
(Continued)

(56) References Cited

U.S. PATENT DOCUMENTS

| 6,375,683 | B1 | 4/2002 | Crozet et al. |
| 7,018,415 | B1 | 3/2006 | McKay |
| 7,771,473 | B2 | 8/2010 | Thramann |
| 8,110,004 | B2 | 2/2012 | Valdevit et al. |
| 9,901,459 | B2 * | 2/2018 | Faulhaber ............. A61F 2/4611 |

(Continued)

FOREIGN PATENT DOCUMENTS

FR    3006168 A1    12/2014

OTHER PUBLICATIONS

Supplementary European Search Report, issued in corresponding European Application No. EP17810942, dated Jan. 2, 2020, 5 pages.
(Continued)

*Primary Examiner* — Marcela I. Shirsat
(74) *Attorney, Agent, or Firm* — Meunier Carlin & Curfman LLC

(57) ABSTRACT

Provided are systems, devices and methods for treating spinal injuries and abnormalities. For example, provided are spinal fusion devices and methods for treating degenerative disc disease using the spinal fusion device.

18 Claims, 5 Drawing Sheets

(51) Int. Cl.
*A61B 17/02* (2006.01)
*A61B 90/00* (2016.01)
*A61F 2/30* (2006.01)

(52) U.S. Cl.
CPC ....... *A61B 2090/031* (2016.02); *A61F 2/4425* (2013.01); *A61F 2002/30261* (2013.01); *A61F 2002/30383* (2013.01); *A61F 2002/30401* (2013.01); *A61F 2002/30471* (2013.01); *A61F 2002/30476* (2013.01); *A61F 2002/30482* (2013.01); *A61F 2002/30556* (2013.01); *A61F 2002/30579* (2013.01); *A61F 2002/30593* (2013.01); *A61F 2002/30601* (2013.01)

(58) Field of Classification Search
CPC .. A61F 2002/30579; A61F 2002/30331; A61F 2002/30471; A61F 2002/30476; A61F 2002/30401; A61F 2002/304; A61F 2002/30367; A61F 2002/4627; A61F 2002/30601; A61B 17/025; A61B 2017/0256; B66F 7/18; B66F 7/26
USPC .......................................... 623/17.11–17.16
See application file for complete search history.

(56) References Cited

U.S. PATENT DOCUMENTS

| | | | |
|---|---|---|---|
| 10,548,743 B2* | 2/2020 | Faulhaber | A61F 2/447 |
| 2006/0069442 A1 | 3/2006 | Michelson | |
| 2008/0243251 A1 | 10/2008 | Stad et al. | |
| 2010/0049324 A1 | 2/2010 | Valdevit et al. | |
| 2011/0251690 A1 | 10/2011 | Berger et al. | |
| 2013/0103154 A1* | 4/2013 | Trieu | A61F 2/447 |
| | | | 623/17.16 |
| 2013/0158669 A1 | 6/2013 | Sungarian et al. | |
| 2014/0094917 A1 | 4/2014 | Salerni | |
| 2015/0057753 A1 | 2/2015 | Barrus et al. | |

OTHER PUBLICATIONS

International Preliminary Report on Patentability dated Dec. 20, 2018, issued in corresponding PCT Application No. PCT/US2017/036376.

International Search Report and Written Opinion issued in related International Application No. PCT/US2017/036376 dated Sep. 11, 2017.

Leva Interbody Devices "Surgical Techniques" Cat # 19-8001 Rev4/15, 2015 Spine Wave Inc.

* cited by examiner

US 11,039,934 B2

EXPANDABLE SPINAL FUSION DEVICE AND METHOD

TECHNICAL FIELD

This disclosure relates to spinal corrective surgery, and more particular to an expandable spinal fusion cage that facilitates fusing a spinal segment into a solid bone mass for treating spine injuries and abnormalities, for example treating degenerative disc disease.

BACKGROUND

The spine includes a plurality of vertebrae arranged in a vertical column. Between each vertebra there is an intervertebral disc that provides a cushion between adjacent vertebrae and transmits force between adjacent vertebrae. Traditionally degenerative disc disease has been treated by surgically removing a diseased disc and inserting an implant in the space vacated by the diseased disc. The implant may be bone or other biocompatible implants. The adjacent vertebrae are then immobilized relative to one another, and then the adjacent vertebrae grow into one solid piece of bone over time. This process can include using a bone graft and a plate to stabilize the implant.

Traditionally, inserting a bone graft involves distracting the disc space and manually keeping the ventral bodies separated. The bone graft or implant is then positioned and a plate is applied over adjacent vertebrae.

Known in the art are expandable fusion cages with inserts wherein the insert is received between an inferior and superior baseplate, like the one described in U.S. Pat. No. 8,110,004. However, the insert is not removable when the cage is in the expanded orientation and thus substantially limits the size of the cavity for which bone graft material may be inserted.

SUMMARY

Provided are expandable spinal fusion devices and methods for treating spinal injuries and abnormalities.

In an example embodiment, an expandable spinal fusion device may include an elongated cam, a first elongated plate, and a locking mechanism. The elongated cam may have a plate body extending along a longitudinal axis. The first elongated plate may include a first proximal end, a first distal end, a first exterior surface, and a first interior surface opposite the first exterior surface. A portion of the first interior surface may be in physical contact with the plate body of the elongated cam. A portion of the first exterior surface may be sized and shaped to interface with a first vertebral body. The first elongated plate may include a second proximal end, a second distal end, a second exterior surface, and a second interior surface opposite the second exterior surface. A portion of the second interior surface may be in physical contact with the plate body of the elongated cam. A portion of the second exterior surface may be sized and shaped to interface with a second vertebral body.

The elongated cam may be adapted to cause the first and second elongated plates to move away from each other upon the elongated cam being rotated about the longitudinal axis such that a relative orientation of the first and second elongated plates is changed from a collapsed orientation to at least one expanded orientation. The locking mechanism may be separate from the elongated cam and adapted to maintain the relative orientation of first and second elongated plates in the at least one expanded orientation such that the elongated cam is removable from the expandable spinal fusion device without causing the first and second elongated plates to return to the collapsed orientation.

The details of one or more embodiments of the disclosure are set forth in the accompanying drawings and the description below. Other features, objects, and advantages of the disclosure will be apparent from the description, drawings, and from the claims.

DESCRIPTION OF DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Figure 1:
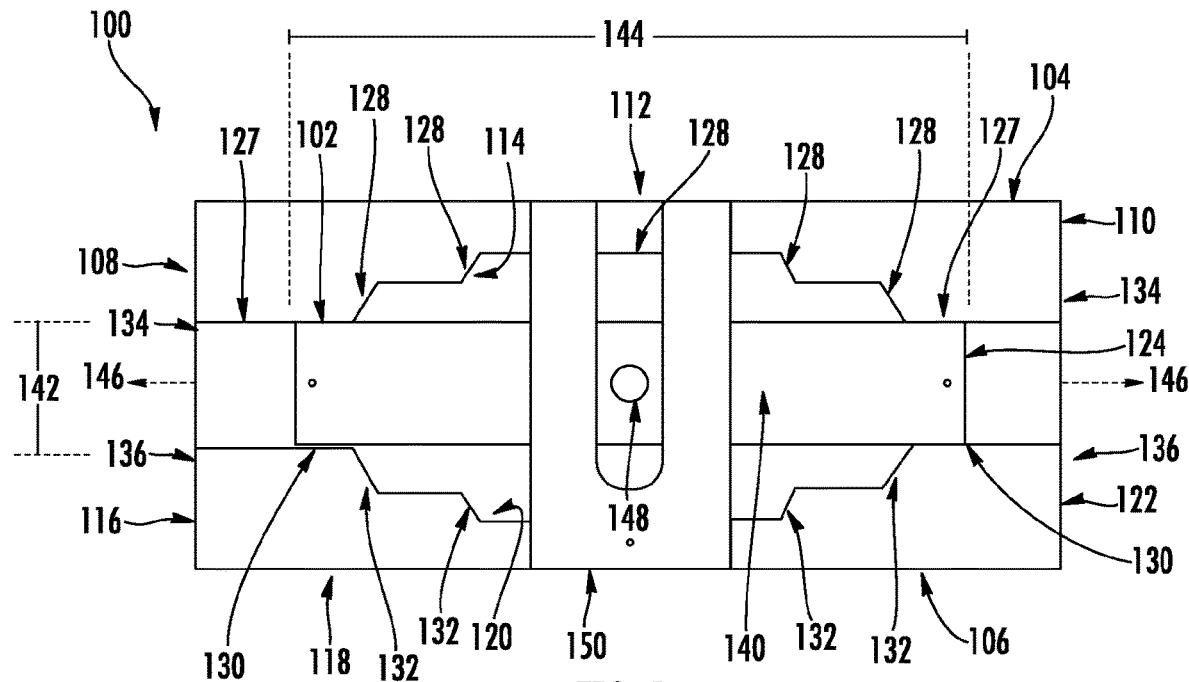
FIG. 1 is a front view of an example expandable spinal fusion device in accordance with the present disclosure, wherein the view shows the expandable spinal fusion device in a collapsed orientation.

The following is a description of several illustrations of expandable spinal fusion devices and methods for treating spinal injuries and abnormalities.

Certain terminology is used herein for convenience only and is not to be taken as a limitation on the present invention. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

FIGS. 1-6 illustrate an example expandable spinal fusion device 100 in accordance with the present disclosure. The example expandable spinal fusion device 100 includes an elongated cam 102, a first elongated plate 104, a second elongated plate 106, and a locking mechanism 107.

Figure 2:
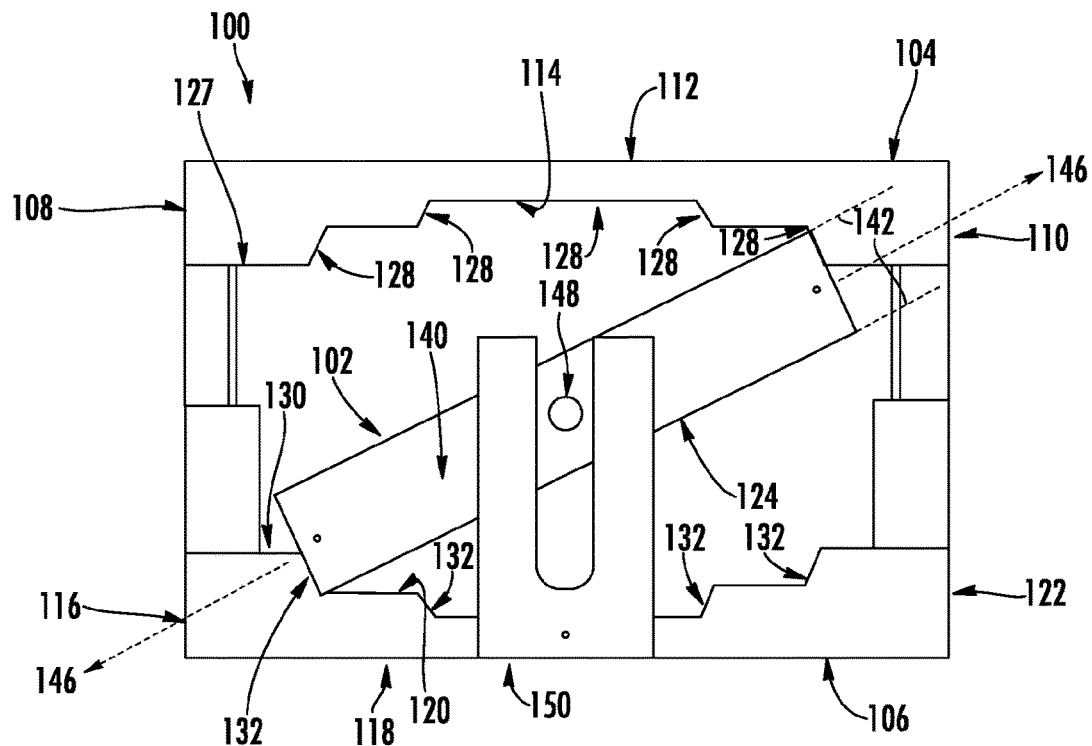
FIG. 2 is another front view of the expandable spinal fusion device of FIG. 1 in accordance with the present disclosure, wherein the view shows the expandable spinal fusion device in a partially extended orientation.
Figure 3:
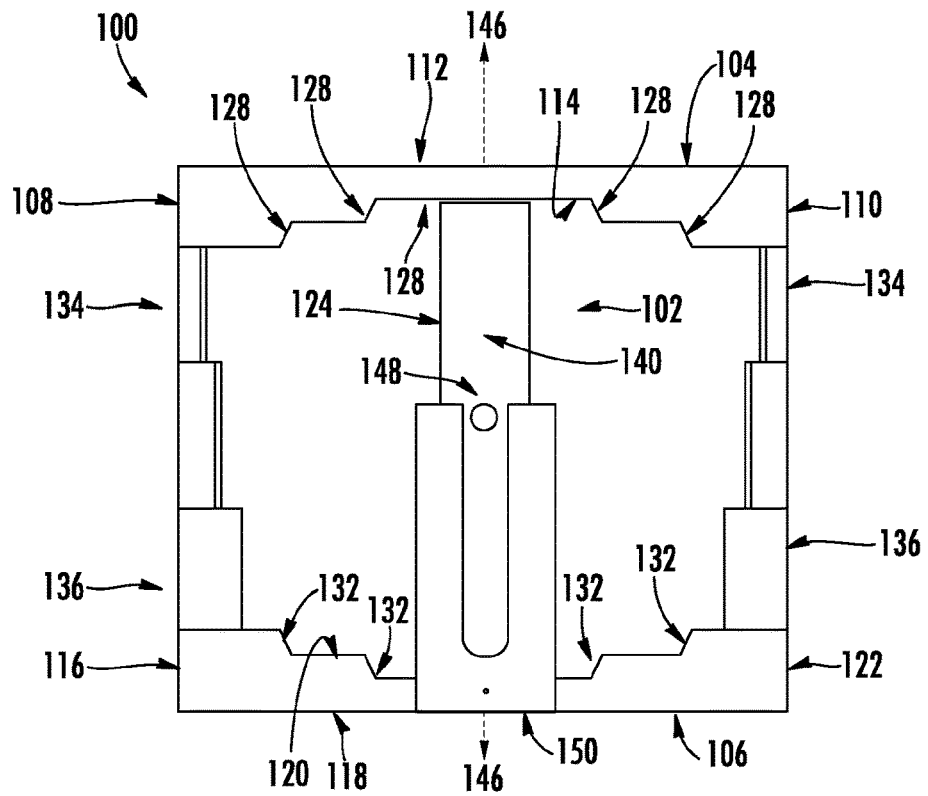
FIG. 3 is another front view of the expandable spinal fusion device of FIG. 1 in accordance with the present disclosure, wherein the view shows the expandable spinal fusion device in a fully extended orientation.
Figure 4:
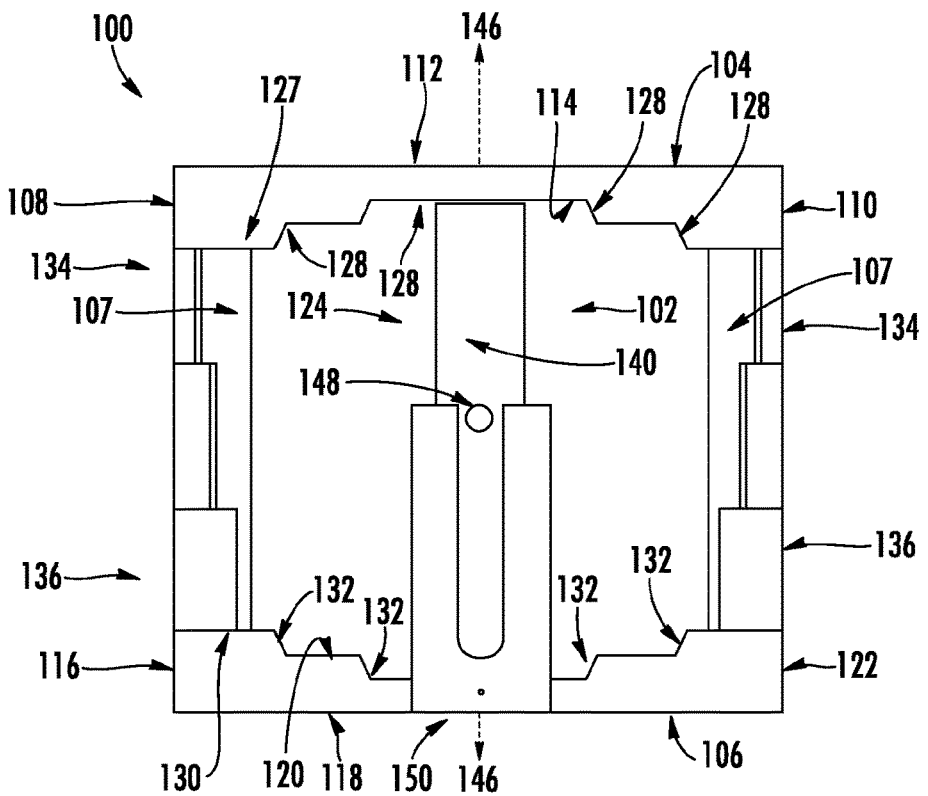
FIG. 4 is another front view of the expandable spinal fusion device of FIG. 1 in accordance with the present disclosure, wherein the view shows the expandable spinal fusion device in a fully extended orientation with a locking mechanism in place.
Figure 5:
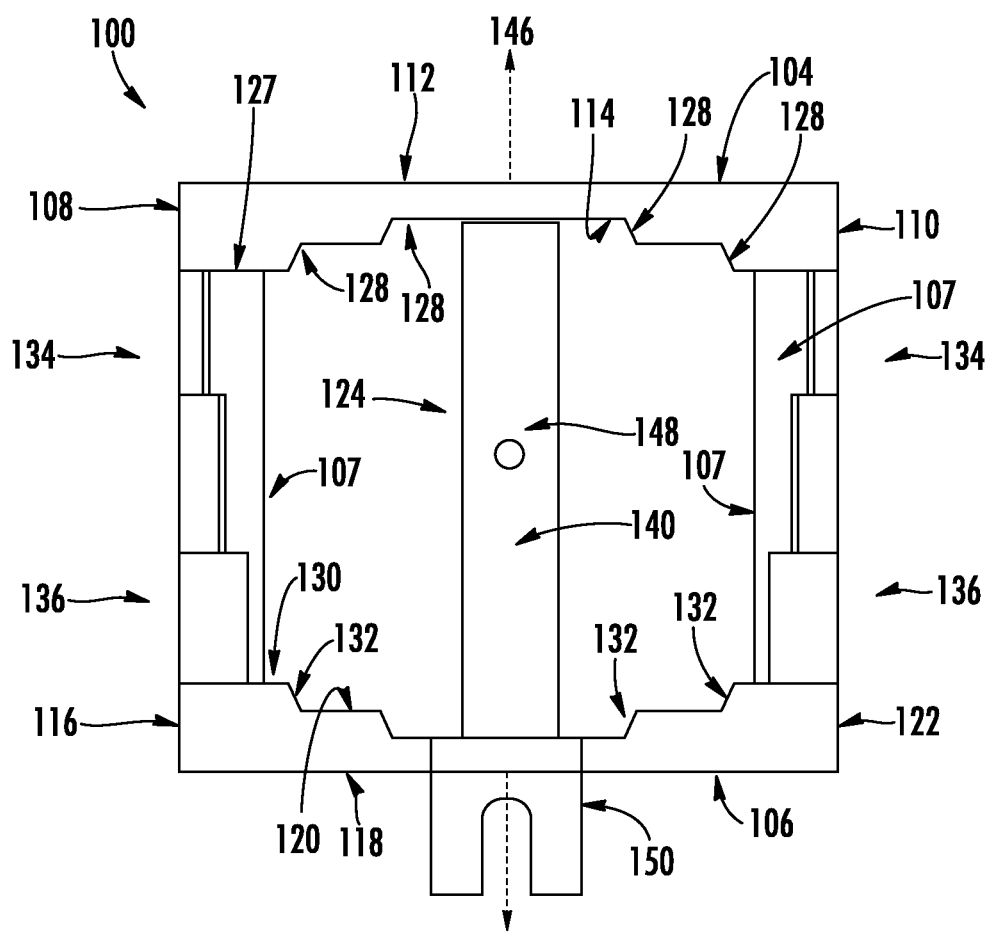
FIG. 5 is another front view of the expandable spinal fusion device of FIG. 1 in accordance with the present disclosure, wherein the view shows the expandable spinal fusion device in a fully extended orientation with a locking mechanism in place and with a retracted front post.

The elongated cam 102 of the example expandable spinal fusion device 100 includes a plate body 124 that extends along a longitudinal axis 126. The plate body 124 can take the form of various suitable shapes. For example, the plate body 124 can be substantially rectangular. Suitable shapes include, for example, an oval, a standard rectangle, a rectangle with rounded edges, and other suitable oblong shapes. The elongated cam 102 is adapted to cause the first and second elongated plates 104, 106, to move away from each other upon the elongated cam 102 being rotated about the longitudinal axis 126 such that a relative orientation of the first and second elongates plates 104, 106, is changed from a collapsed orientation to at least one expanded orientation. FIG. 1 shows an example of a collapsed orientation. FIG. 2 shows an example of an expanded orientation, in particular a partially expanded orientation. FIGS. 3-5 show an example of a fully expanded orientation.

The first elongated plate 104 of the example expandable spinal fusion device 100 includes a first proximal end 108, a first exterior surface 112, a first interior surface 114 opposite the first exterior surface 112, and a first distal end 110. The first exterior surface 112 can be sized and shaped to interface with a first vertebral body. The first interior surface 114 includes a portion 127 that makes physical contact with the plate body 124 of the elongated cam 102 when in a collapsed orientation, for example, the collapsed orientation of FIG. 1. In certain embodiments, the first interior surface 114 further includes one or more recesses 128 sized to fit and secure the plate body 124 to the first elongated plate 104 in one or more of the various disclosed expanded orientations, for example, the partial expanded orientation shown in FIG. 2, and the fully expanded orientation shown in FIGS. 3-5.

Similarly, the second elongated plate 106 of the example expandable spinal fusion device 100 includes a second proximal end 116, a second exterior surface 118, a second interior surface 120 opposite the second exterior surface 118, and a second distal end 122. The second exterior surface 118 can be sized and shaped to interface with a first vertebral body. The first and second elongated plates 104, 106, can come in various shapes and sizes. For example, the first elongated 104 plate and/or the second elongated plate 106 can be substantially rectangular. The second interior surface 120 includes a portion 130 that makes physical contact with the plate body 124 of the elongated cam 102 when in a collapsed orientation, for example, the collapsed orientation of FIG. 1. In certain embodiments, the second interior surface 120 further includes, one or more recesses 132 sized to fit and secure the plate body 124 to the second elongated plate 106 in one or more of the various disclosed expanded orientations, for example, partial expanded orientation of FIG. 2, and the fully expanded orientation of FIGS. 3-5.

In certain embodiments the first and second elongated plates 104, 106 further include pairs of side sections 134, 136. For example, the first elongated plate 104 can include a first pair of side sections 134 and the second elongated plate can include a second pair of side sections 136. The first pair of side sections 134 can be adapted to engage the second pair of side sections 136 to facilitate a moveable interconnection between the first elongated plate 104 and the second elongated plate 106. For example, the first and second pairs of side sections 134, 136, can comprise reciprocal parts of a telescoping coupling. The pairs of side sections 134, 136, can be aligned is various suitable ways, including, for example, being substantially perpendicular to the first exterior surface 112 and/or the first interior surface 114. In certain embodiments, the first and second exterior surfaces 112, 118, have a distance between them that is less than or equal to 6 millimeters when in the collapsed orientation. Additionally, in certain embodiments, the first and second exterior surfaces 112, 118, has a distance between them that is greater than or equal to 10 millimeters when in an expanded orientation. Other suitable ranges and distances can be selected.

The locking mechanism 107 of the example expandable spinal fusion device 100 maintains the relative orientation of the first and second elongated plates 104, 106, such that the elongated cam 102 can be removed from the expandable spinal fusion device 100 without causing the first and second elongated plates 104, 106, to return to a previous orientation, for example, the collapsed orientation. Suitable locking mechanisms include, for example, stabilizers, clips, spacers, or other structures that can form a friction fit between the first interior surface 114 and the second interior surface 120. FIGS. 4-5 illustrate one such example, a pair of narrow rectangular spacers 107 that have been placed between the first interior surface 114 and the second interior surface 120. The locking mechanism 107 can be placed in the spinal fusion device 100 via manual or mechanical means. For example, one may employ an insertion tool 800 like the one shown in FIG. 8 and described in detail below.

In certain embodiments, the plate body 124 of the elongated cam 102 further includes a distal end 138 and a proximal end 140. The distal end 138 and/or the proximal end 140 of the plate body 124 can include a height 142 and a width 144 in which the height 142 is less than the width 144. The width 144 can define a first axis 146 that is generally parallel to the first and second interior surfaces 114, 120, when in the collapsed orientation, and generally perpendicular to the first and second interior surfaces 114, 120, when in the at least one expanded orientation. Additionally, in certain embodiments the length of the plate body 124 is sized in such a way so that a length measured between the distal end 138 and the proximal end 140 of the plate body 124 is substantially equal to at least a length measured between the first distal end 110 and the first proximal end 108 or a length measured between the second distal end 122 and the second proximal end 116. In other words, the length of the plate body 124 can be the same as the length of the first and second elongated plates 104, 106.

Figure 8:
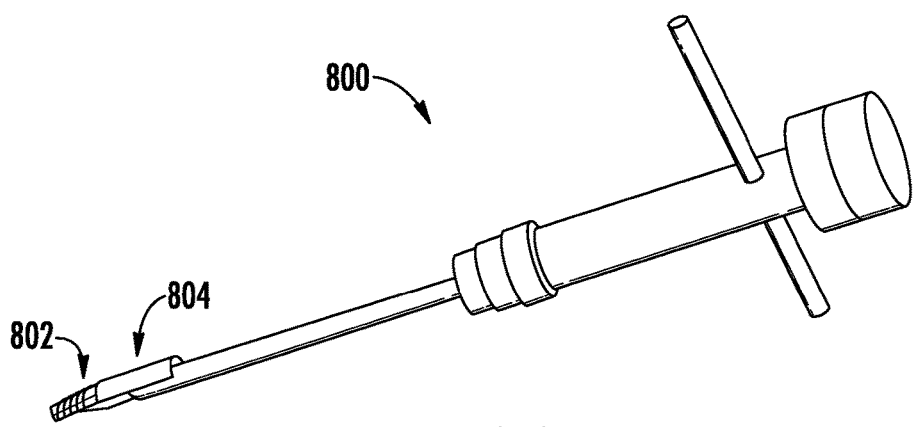
FIG. 8 is a perspective view of an example insertion tool in accordance with the present disclosure.

In certain embodiments, the distal end 138 and/or the proximal end 140 of the plate body 124 further include an aperture 148 that is adapted to receive an insertion tool for facilitating the rotation of the elongated cam 102. One suitable aperture is a screw hole. FIG. 8 illustrates an example insertion tool 800 which can be used to facilitate insertion of the expandable spinal fusion device 100, as well as facilitate the rotation and extraction of the elongated cam 102. In use, one may couple the insertion tool 800 to the aperture 148, rotate the elongated cam 102 about the longitudinal axis 126 to move the first and second elongated plates 104, 106, away from each other, and then after securing the relative orientation using a locking mechanism 107 separate from the elongated cam 102, the elongated cam 102 can be removed by pulling the elongated cam 102 outwards along the longitudinal axis 126. The insertion tool 800 can include, for example, a screwdriver head 802 or other suitable heads or structure for engaging the aperture. The insertion tool 802 can further include an outer sliding sleeve which facilities insertion of the locking mechanism 107 in a cavity between the first and second elongated plates 104, 106.

In certain embodiments, the expandable spinal fusion device 100 further includes a guide post 150 and the elongated cam 102 further includes an axial protrusion 151 that projects outwardly from distal end 138 and/or the proximal end 140 of the plate body 124. The guide post 150 provides the spinal fusion device 100 a means for guiding and retraining displacement of the axial protrusion 151 during at least insertion and rotation. For example, the guide post 150 can help maintain the longitudinal axis 126 of the elongated cam 102 allied with the first and/or second elongated plates 104, 106. The guide post 150 can include a release switch for allowing the guide post to pivot away from the elongated cam to free the elongated cam for subsequent removal. FIG. 5 illustrates an example of the pivoting described above. The insertion tool 800 can also be used for actuating the switch.

Figure 6:
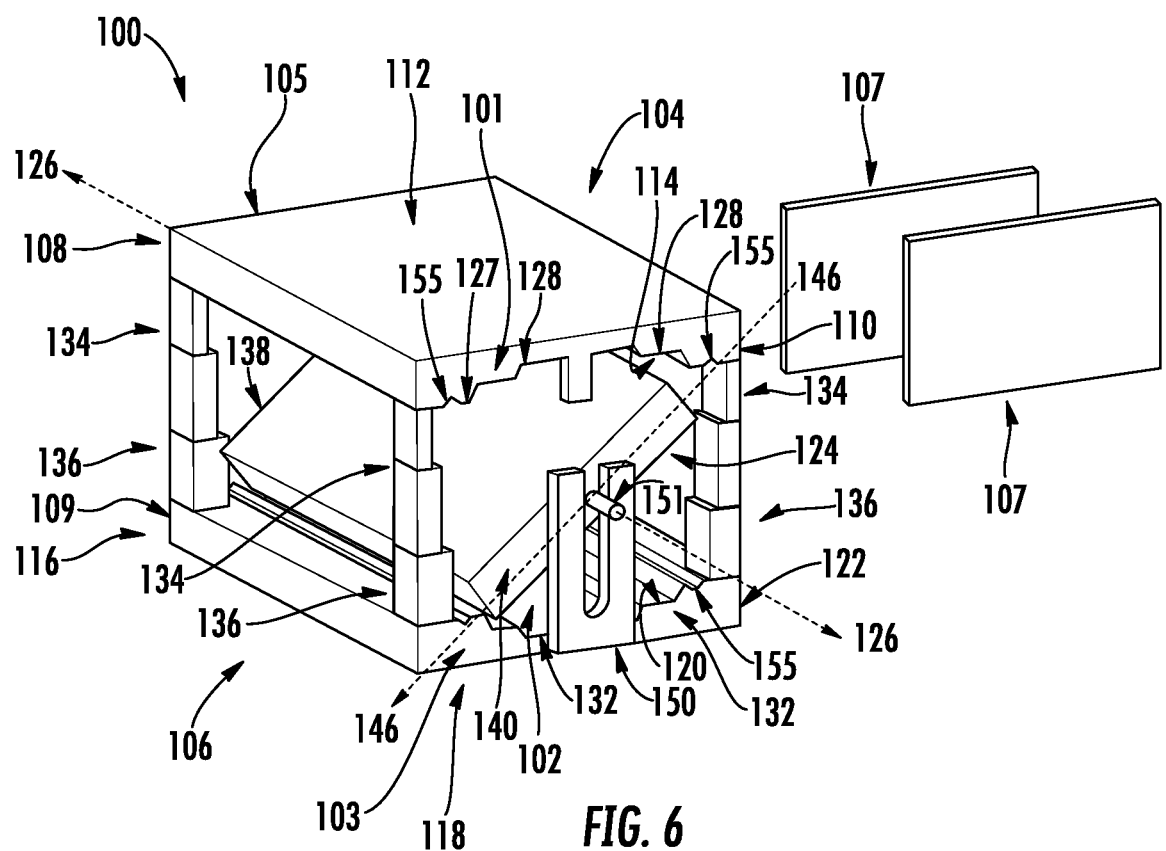
FIG. 6 is a perspective view of the expandable spinal fusion device of FIG. 1 in accordance with the present disclosure.

FIG. 6 illustrates an example embodiment where the interior surface 114 and interior surface 120 include grooved slots 155 that traverse from the first proximal surface 101 of the first elongated plate 104 and second proximal surface 103 of the second elongated plate 106, to the first distal surface 105 of the first elongated plate 104 and second distal surface 109 of the second elongated plate 106. Grooved slots 155 can be used to attach one or more locking mechanisms 107 like the ones described above.

Figure 7:
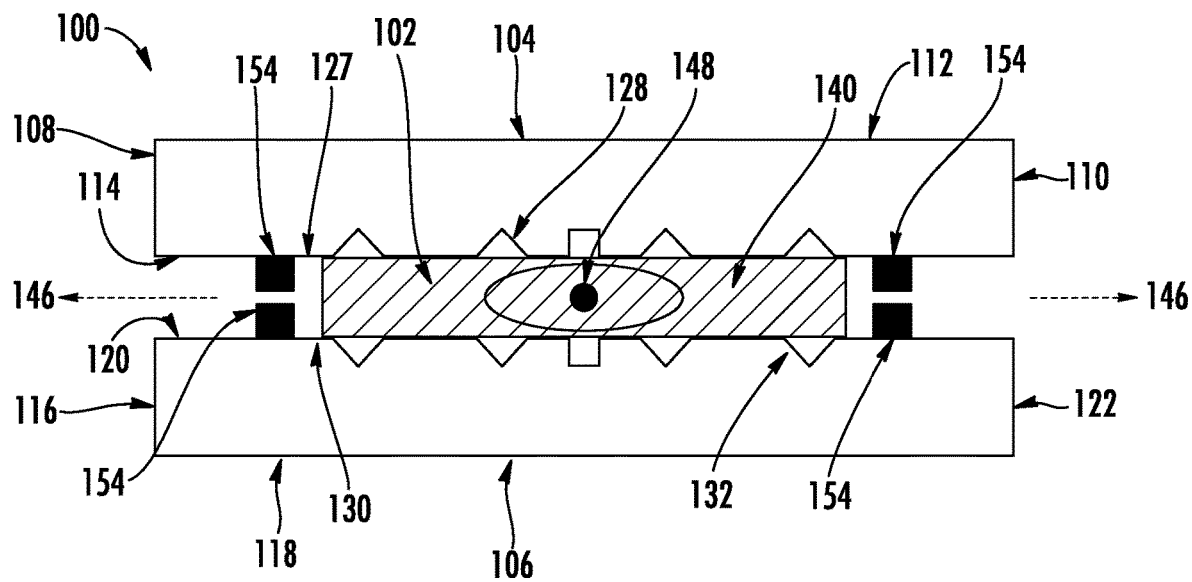
FIG. 7 is a front view of another example expandable spinal fusion device in accordance with the present disclosure.

FIG. 7 illustrates an example embodiment where the expandable spinal fusion device 100 further includes a plurality of torque restricting tabs 154. In particular, the first elongated plate 104 includes two or more torque restricting tabs 154 that project out from the first interior surface 114 towards the second interior surface 120. In certain embodiments, the second elongated plate 106 further includes two or more torque restricting tabs 154 that project out from the second interior surface 120 towards the first interior surface 114. In certain embodiments the first elongated plate 104 further includes at least one torque restricting tab 154 that projects out from the first interior surface 114 towards the second interior surface 120, and the second elongated plate 106 includes at least one torque restricting tab 154 that projects out from the second interior surface 120 towards the first interior surface 114.

Also provided are methods for fusing a vertebral segment using the expandable spinal fusion devices disclosed herein. An example method includes positioning the expandable spinal fusion device 100 into an intervertebral disc space between adjacent vertebral bodies in a spine, and then changing a relative orientation of the first and second elongated plates from a collapsed orientation to at least one expanded orientation by rotating the elongated cam about the longitudinal axis 126. See for example FIGS. 1-4. The expandable spinal fusion device 100 can be placed manually or through the use of a separate device, for example, the insertion tool 800 shown in FIG. 8. As explained above, the insertion tool 800 can also be used to rotate the elongated cam 102 about the longitudinal axis 126.

The example method further includes locking the expandable fusion device 100 in the at least one expanded orientation via a locking mechanism 107 and then removing the elongated cam 102 from the expandable spinal device 100. See for example FIGS. 5-6. As explained above, the locking mechanism 107 can be a separate device from the elongated cam 102 and can be adapted to maintain the relative orientation of the first and second elongated plates 104, 106 in at least one expanded orientation such that the elongated cam 102 is removable from the expandable spinal fusion device 100 without causing the first and second elongated plates 104, 106 to return to a previous orientation, for example, the collapsed orientation. In certain embodiments that include a guide post 150, the guidepost 150 can then be pivoted away. The insertion tool 800 described above can be used to remove the elongated cam 102 from the expandable fusion device 100. The example method can further include inserting bone graft material between the first elongated plate 104 and the second elongated plate 106. The graft material can be inserted, for example, after the removal of the elongated cam 102.

The expandable spinal fusion device 100 can be created from various suitable materials, including for example, biocompatible materials like titanium and polyethylene ketone. The parts can be created through 3D printing as well through other processes known to those having ordinary skill in the art.

A number of embodiments of the invention have been described. Nevertheless, it will be understood that various modifications may be made without departing from the spirit and scope of the invention. Accordingly, other embodiments are within the scope of the following claims.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a method is disclosed and discussed each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the materials for which they are cited are hereby specifically incorporated by reference in their entireties.

What is claimed is:

1. An expandable spinal fusion device comprising:
    an elongated cam having a plate body extending along a longitudinal axis;
    a first elongated plate comprising a first proximal end, a first distal end, a first exterior surface, and a first interior surface opposite the first exterior surface, at least a portion of the first interior surface being in physical contact with the plate body of the elongated cam, wherein at least a portion of the first exterior surface is sized and shaped to interface with a first vertebral body;
    a second elongated plate comprising a second proximal end, a second distal end, a second exterior surface, and a second interior surface opposite the second exterior surface, at least a portion of the second interior surface being in physical contact with the plate body of the elongated cam, wherein at least a portion of the second exterior surface is sized and shaped to interface with a second vertebral body;
    wherein the elongated cam is adapted to cause the first and second elongated plates to move away from each other upon the elongated cam being rotated about the longitudinal axis such that a relative orientation of the first and second elongated plates is changed from a collapsed orientation to at least one expanded orientation; and
    a locking mechanism, separate from the elongated cam, that is adapted to maintain the relative orientation of first and second elongated plates in the at least one expanded orientation such that the elongated cam is removable from the expandable spinal fusion device without causing the first and second elongated plates to return to the collapsed orientation,
    wherein the plate body of the elongated cam further comprises a distal end and a proximal end, wherein at least the proximal end or the distal end of the plate body includes a height and a width, wherein the height is less than the width, wherein the width defines a first axis, the first axis being parallel to the first and second interior surfaces when in the collapsed orientation and perpendicular to the first and second interior surfaces when in the at least one expanded orientation, wherein the elongated cam is longitudinally removable when the elongated cam is rotated until the first axis is perpendicular to the first and second interior surfaces.

2. The expandable spinal fusion device of claim 1, wherein the plate body of the elongated cam is rectangular.

3. The expandable spinal fusion device of claim 1, wherein at least the first elongated plate or the second elongated plate is rectangular.

4. The expandable spinal fusion device of claim 1, wherein the first elongated plate further comprises a first pair of side sections and the second elongated plate further comprises a second pair of side sections, wherein the first pair of sides are adapted to engage the second pair of sides to facilitate a moveable interconnection between the first elongated plate and the second elongated plate.

5. The expandable spinal fusion device of claim 4, wherein the first pair of sides are perpendicular to at least the first exterior surface or the first interior surface.

6. The expandable spinal fusion device of claim 4, wherein the second pair of sides are perpendicular to at least the second exterior surface or the second interior surface.

7. The expandable spinal fusion device of claim 1, wherein a distance between the first and second exterior surfaces in the collapsed orientation is less than or equal to 6 millimeters.

8. The expandable spinal fusion device of claim 1, wherein a distance between the first and second exterior surfaces in the at least one expanded orientation is greater than or equal to 10 millimeters.

9. The expandable spinal fusion device of claim 1, wherein at least the distal end or the proximal end of the plate body includes an aperture that is adapted to receive an insertion tool for facilitating the rotation of the elongated cam.

10. The expandable spinal fusion device of claim 9, wherein the aperture comprises a screw hole and the insertion tool includes a screwdriver head.

11. The expandable spinal fusion device of claim 1, wherein a length measured between the distal end and the proximal end of the plate body is equal to at least a length measured between the first distal end and the first proximal end or a length measured between the second distal end and the second proximal end.

12. The expandable spinal fusion device of claim 1, wherein the first elongated plate further comprises at least two torque restricting tabs that project out from the first interior surface.

13. The expandable spinal fusion device of claim 1, wherein the second elongated plate further comprises at least two torque restricting tabs that project out from the second interior surface.

14. The expandable spinal fusion device of claim 1, wherein the first elongated plate further comprises at least a first torque restricting tab that projects out from the first interior surface, and wherein the second elongated plate further comprises at least a second torque restricting tab that projects out from the second interior surface.

15. The expandable spinal fusion device of claim 1, wherein the locking mechanism comprises one or more spacers that form a friction fit between the first interior surface and the second interior surface, wherein the spacers are positioned lateral to the elongated cam.

16. A method of fusing a vertebral segment comprising:
    positioning an expandable spinal fusion device in an intervertebral disc space between adjacent vertebral bodies in a spine, the expandable spinal fusion device comprising:
        an elongated cam having a plate body extending along a longitudinal axis;
        a first elongated plate comprising a first proximal end, a first distal end, a first exterior surface, and a first interior surface opposite the first exterior surface, at least a portion of the first interior surface being in physical contact with the plate body of the elongated cam, wherein at least a portion of the first exterior surface is sized and shaped to interface with a first vertebral body;
        a second elongated plate comprising a second proximal end, a second distal end, a second exterior surface, and a second interior surface opposite the second exterior surface, at least a portion of the second interior surface being in physical contact with the plate body of the elongated cam, wherein at least a portion of the second exterior surface is sized and shaped to interface with a second vertebral body;
    changing a relative orientation of the first and second elongated plates from a collapsed orientation to at least one expanded orientation by rotating the elongated cam about the longitudinal axis;

locking the expandable spinal fusion device in the at least one expanded orientation via a locking mechanism, wherein the locking mechanism is separate from the elongated cam and is adapted to maintain the relative orientation of the first and second elongated plates in the at least one expanded orientation such that the elongated cam is removable from the expandable spinal fusion device without causing the first and second elongated plates to return to the collapsed orientation; and after locking the expandable spinal fusion device in the at least one expanded orientation, removing the elongated cam from the expandable spinal fusion device, wherein the plate body of the elongated cam further comprises a distal end and a proximal end, wherein at least the proximal end or the distal end of the plate body includes a height and a width, wherein the height is less than the width, wherein the width defines a first axis, the first axis being parallel to the first and second interior surfaces when in the collapsed orientation and perpendicular to the first and second interior surfaces when in the at least one expanded orientation, wherein removing the elongated cam comprises rotating the elongated cam until the first axis is perpendicular to the first and second interior surfaces and then longitudinally extracting the elongated cam.

17. The method of claim 16 further comprising inserting bone graft material between the first elongated plate and the second elongated plate.

18. The method of claim 16, wherein the bone graft material is inserted after the removing of the elongated cam.

* * * * *